United States Patent [19]

Marshall

[11] Patent Number: 4,682,043
[45] Date of Patent: Jul. 21, 1987

[54] OBTAINING UNIFORMITY OF RESPONSE IN ANALYTICAL MEASUREMENT IN A NEUTRON-CAPTURE-BASED ON-LINE BULK-SUBSTANCE ELEMENTAL-ANALYZER APPARATUS

[76] Inventor: J. Howard Marshall, 145 Hurlbut, Apt. 305, Pasadena, Calif. 91105

[21] Appl. No.: 61,833

[22] Filed: Jul. 30, 1979

Related U.S. Application Data

[63] Continuation of Ser. No. 866,488, Jan. 3, 1978.

[51] Int. Cl.$^4$ ............................................. G01F 23/00
[52] U.S. Cl. ............................. 250/358.1; 250/359.1; 250/390
[58] Field of Search ............... 250/358 R, 358 P, 359, 250/390, 391, 392, 432, 435, 453

[56] References Cited

U.S. PATENT DOCUMENTS

| | | | |
|---|---|---|---|
| 3,053,388 | 9/1962 | Tittle | 250/359 |
| 3,082,323 | 3/1963 | Chope et al. | 250/358 R |
| 4,028,267 | 6/1977 | Christell et al. | 250/359 |

*Primary Examiner*—Janice A. Howell
*Attorney, Agent, or Firm*—James E. Brunton

[57] ABSTRACT

In an apparatus for neutron-capture-based on-line elemental analysis of bulk substances, an improved uniformity of response of analytical measurement will make the apparatus less sensitive to segregations that occur in moving streams of the bulk substance. The apparatus incorporates a measurement volume having a substantially-square cross-section with rounded corners in the plane perpendicular to the direction of flow in order to exclude the bulk substance from regions of unusual sensitivities and to facilitate the orientation of the instrument for minimum sensitivity to segregations in the bulk substance. The apparatus also includes a plurality of neutron sources which expose the analyzed bulk substance momentarily contained within the apparatus to a flux of neutrons. The apparatus also provides for the use of neutron reflectors to increase the neutron flux near the sides of the measurement volume, further improving the uniformity of measurement. The analyzed substance captures some of the neutrons by (n,$\gamma$) reactions, producing prompt gamma rays which are detected to provide the composition measurement. The use of multiple sources causes the neutron flux to rise instead of fall near the sides of the volume containing the bulk substance compared to the center of the volume, and flux variations can be made to cancel solid-angle variations to produce a more-uniform response over a substantial portion of the measurement volume. Similarly the use of multiple gamma-ray detectors can also reduce these solid-angle variations, improving measurement uniformity, particularly if the measurement volume is large because of material-flow requirements.

8 Claims, 2 Drawing Figures

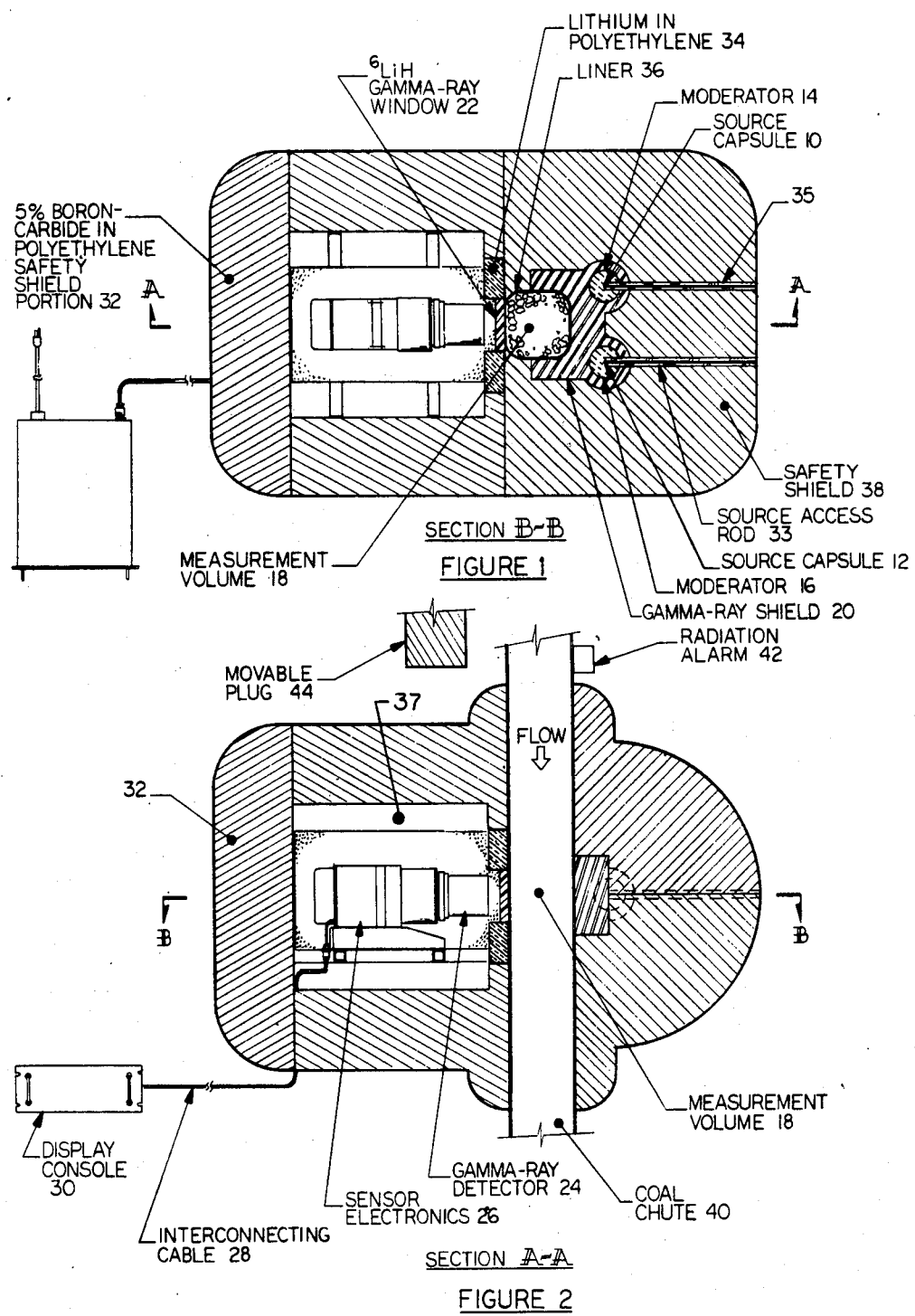

OBTAINING UNIFORMITY OF RESPONSE IN ANALYTICAL MEASUREMENT IN A NEUTRON-CAPTURE-BASED ON-LINE BULK-SUBSTANCE ELEMENTAL-ANALYZER APPARATUS

This is a continuation of application Ser. No. 866,488, filed Jan. 3, 1978.

BACKGROUND OF THE INVENTION

1. Field of the Invention

This invention generally relates to nuclear meters, and more particularly to improvements in neutron-capture-based elemental analyzers leading to an increased uniformity of response in on-line analytical measurements of bulk substances.

2. Description of the Prior Art

The rising cost of fuels, coupled with the need to avoid atmospheric pollution when burning them, has led to the requirement that their composition be known at various points in the fuel-preparation cycle. For example, because of the scarcity of low-sulfur crude oils and the cost of sulfur removal, the value of fuel oil increases significantly as its sulfur content becomes lower, indicating that accurate fuel-oil blending to a fixed sulfur level consistent with allowable amounts of pollution is both cost effective and an efficient utilization of increasingly-scarce hydrocarbons. Furthermore, precise knowledge of the heat content of fuel oil allows furnaces and boilers to be operated in a more-efficient manner. In addition, knowledge of the amount of sulfur and other contaminants such as vanadium and nickel in various hydrocarbon streams can help prevent the poisoning of catalysts used in oil refineries, avoiding costly shut downs.

In the case of coal, sulfur content is generally higher than that of oil, making the pollution problem even more severe. As a result, expensive coal-cleaning plants, stack-gas scrubbers and precipitators are necessary, all of which can be operated more efficiently if the coal composition is known on a real-time, on-line basis. Efficient boiler operation also benefits from this composition measurement, and knowing the composition of the ash in the coal can be used to avoid boiler slagging, which is a costly problem that is generally absent for fuel oil.

Particularly in the case of coal, but also for oil, these composition measurements have to be made on inhomogeneous substances with high mass flow rates and variable compositions. Thus, this measurement should continuously reflect the average composition of the bulk substance, and response times should be fast enough to permit effective process control. Generally the latter requirement implies a speed of response ranging from a few minutes up to an hour.

A technique which can satisfy these requirements can often be used in applications which do not involve fuels or their derivatives. For example, it could measure the nitrogen content of wheat in order to determine the amount of protein present, which in turn is related to food value. Thus, the measurement of fuels is illustrative only and is not essential to this invention, which applies to all measurements of bulk substances by the techniques to be described hereinafter.

Several methods for composition measurement are known in the prior art, the most obvious one being sampling following by chemical analysis. This technique provides most present data on the composition of various bulk substances. Unfortunately sampling is inherently inaccurate because of the lack of homogeneity of bulk materials, and large continual expenditures for manpower, sampling devices and chemical-analysis equipment are required to provide response times which at best could approach one hour. These disadvantages lead to the consideration of other techniques which are faster, more subject to automatic operations and more of an on-line continuous bulk measurement.

One technique often used in industrial environments for elemental analysis involves X-ray fluoresence. This technique relies on the fact that each atom emits X-rays with distinct and well-known energies when external radiations disturb its orbital electrons. Unfortunately, sulfur, which is an interesting element from the standpoints of air pollution and catalyst poisoning, emits mostly 2-keV X-rays, which can only traverse about 0.1 mm of a typical fuel. Iron, which is one of the elements generating the highest-energy X-rays in coal, produces mostly a 6-keV X-ray, which also cannot escape from any appreciable amount of coal or other nongaseous fuel. Thus, the use of X-ray fluoresence for other than gaseous materials requires either the preparation of very clean surfaces truly representative of the bulk material or the vaporization of a sample in an atmosphere which does not confuse the measurement. In either case, a difficult sample-preparation problem compounds the errors associated with X-ray fluorescence itself.

A second technique usually involving X-rays which are more penetrating is X-ray absorption. In this case one measures the differences in the absorption or scattering of X-rays caused by changes in the amounts of certain elements. In the case of relatively-pure hydrocarbons such as refined fuel oil, this technique can provide a useful measurement of sulfur content because sulfur at X-ray energies near 22 keV can have a predominant effect on the X-ray absorption. This predominance, however, is dependent on the lack of most of the metals which are present in coal and may also be present in oil. In addition, 22-keV X-rays only penetrate about 2 mm in most non-gaseous fuels, making sampling still a requirement. Moreover, this technique is generally limited to measuring only one of several potentially-interesting elements, and the measurement of the relative amount of many different elements in a complex mixture such as coal becomes difficult.

Nonetheless, nuclear techniques in general remain attractive because they often can be automated and in principal do not require actual manipulation of the bulk material itself. The problems with X-ray fluorescence and absorption arise partly because the Associated radiations are not sufficiently penetrating. However, because the energetic gamma rays produced by the capture of thermal neutrons will penetrate over 100 mm of most fuels, an analysis technique based on them can provide an accurate, continuous, on-line measurement of the elemental composition of bulk substances without sampling.

This technique is based on the fact that almost all elements when bombarded by slow neutrons capture these neutrons at least momentarily and form a compound nucleus in an excited state. Usually the prompt emission of one or more gamma rays with energies and intensities which are uniquely characteristic of the capturing nucleus dissipates most of this excitation energy. Because these prompt gamma rays often have energies in the 2- to 11-MeV range, they can penetrate substantial quantities of material. Thus, for those isotopes with significant capture cross sections and prominent gamma-ray lines, measurement of prompt gamma rays can be used to determine in an on-line, real-time manner the quantity of most of the elements present in bulk substances, which can be flowing through the analyzer.

The above emphasis on thermal neutrons reflects the fact that for most elements the cross section for neutron capture is approximately proportional to the reciprocal of the square root of the neutron energy. Thus, almost all neutron capture occurs at the lowest neutron energies, which happen when the neutrons are in thermal equilibrium with the nuclei of the surrouding medium. As a result, the thermal-neutron-capture cross sections characterize the expected prompt-gamma-ray spectra. These gamma-ray spectra are particularly amenable to simple theoretical interpretation using well-known thermal-neutron-capture cross sections, making automatic operation a feasible concept.

However, because isotopic and other neutron sources generally produce neutrons with average energies of at least several MeV, "moderation" or "thermalization" processes must reduce neutron energies by over eight orders of magnitude in order for them to reach the thermal region near 0.025 eV. Collisions with hydrogen nuclei, which have a mass essentially the same as that of the neutron and a large scattering cross section, are the most effective means for neutron moderation, although collisions with other elements will moderate neutrons to some degree. Because the neutrons move between collisions, the volume of material exposed to significant neutron fluxes can have a considerable extent, which depends mostly on the amount of hydrogen present. Because the thermal neutrons are produced continuously by moderation of the more-energetic neutrons and then diffuse throughout this moderation volume, the substance being measured is sampled over a large extent, providing the bulk measurement.

Although these techniques have been used in the laboratory under controlled conditions, their implementation in an automatic, on-line instrument placed in an industrial environment presents unique problems which prior-art instruments have not solved. One of these problems arises when the instrument must measure accurately substances with compositions which vary within the measurement volume. One such non-uniform material may occur when coal with various particle sizes of different compositions flows through a chute or channel passing through the instrument. Often in this case the coal particles will differentially segregate along the chute walls so that the elemental composition depends upon position within the measurement volume. Only if the instrument has a response which is independent of position within the measurement volume will it measure correctly the average composition of the bulk substance. Incomplete mixing of fluids or slurries could produce the same problems as illustrated above for solid coal, again leading to the need for a uniform response or measurement sensitivity.

In the known prior art, a single neutron source was located in the center of a coal chute passing through the measurement volume, and a single gamma-ray detector, which was located outside of the chute, was used to measure the energy spectrum of the capture gamma rays. In the plane passing through the center of the source and detector, the measurement sensitivity in this configuration varied both along the source-detector line and perpendicular thereto. Three major effects led to these sensitivity variations.

First, the neutron flux decreased as the distance from the source increased, and this flux had to fall substantially at the sides of the chute compared to its center in order to have an acceptable number of neutrons escaping into the detector. Because the probability of producing a gamma ray is proportional to the flux of thermal neutrons, the production probability per unit volume therefor also had to be substantially less at the sides of the chute than at its center.

Second, the solid angle subtended by the detector for each small volume in the coal chute is less for those volumes distant from the detector than for those closer to the detector. As a result, the probability that a gamma ray emitted from such a volume reached the detector decreased for volumes near the source or the far wall of the chute, and for those volumes removed from the source-detector line, compared to volumes on the source-detector line and near the detector side of the chute.

Third, the probability that a gamma ray moving toward the detector can travel from the region where it was produced to the detector without interacting decreases as the distance which it must travel increases. Thus, the measurement sensitivity, which was determined primarily by the gamma rays which did not interact, was less for regions near the source of the far wall of the coal cute compared to regions near the detector.

In these prior-art instruments all of these effective combined to make the sensitivity at the side of the chute on the opposite side of the source as the detector considerably less than the sensitivity in the volume between the source and the detector. However, if the neutron source is located outside of the measurement volume as described in another application for a U.S. patent, Ser. No. 808,106, filed on June 21, 1977 by the inventor herein, then the measurement can be confined to the volume between the source and the detector, resulting in improved uniformity. However, unless the techniques of this invention are also employed, the uniformity of sensitivity may still be insufficient to measure accurately segregated, inhomogeneous substances.

For example, if only a single source and detector are used, both the neutron flux and the solid angle are lowest at the sides of the chute compared to its center along a direction perpendicular to the source-detector line. Furthermore the amount of scattering material through which the gamma rays produced at the sides of the chute must travel to reach the detector is greater, adding to reduced sensitivities at the chute sides compared to its center. This effect becomes more severe as the chute becomes larger, particularly if neutron-absorbing materials or open spaces surround the chute and further depress the thermal-neutron flux at the chute sides. Large chute sizes may result from high mass flow rates or from other geometrical constraints imposed by the industrial environment and various properties of the substance being analyzed.

SUMMARY OF THE INVENTION

Applicant herein has conceived of several improvements for reducing these sensitivity variations in the elemental-analyzer apparatus, and these improvements can be applied either separately or in combination. One technique involves the use of two or more neutron sources which are located such that the neutron flux increases at the sides of the measurement volume compared to the flux at the center. If the number and spacing of the sources are correctly chosen, then this flux increase can compensate for the reduced solid angle and gamma-ray transmission which occur at the sides. As a result, the sensitivity along lines parallel to the face of the detector can be made more uniform.

Similarly multiple gamma-ray detectors can also be used to accomplish the same result. In this case the solid angle and gamma-ray transmission can be enhanced near the sides of the measurement volume compared to its center. The combination of multiple sources with multiple detectors can produce an even-more-uniform measurement sensitivity particularly for large measurement volumes. In addition multiple detectors will measure more of the capture gamma rays and can tolerate higher total counting rates, leading to a more efficient use of neutrons and to a faster speed of response.

The flux at the sides of the measurement volume can be increased by still other means. For example, a smaller measurement volume has a smaller sensitivity variation than one with a larger cross-sectional area. Eliminating low-sensitivity regions, such as the corners of a coal chute, from the measurement volume also improves uniformity. In addition surrounding the measurement volume with a material which scatters neutrons without absorbing many of them will reflect neutrons back into the measurement volume, thus increasing the flux at the sides and improving the efficiency of neutron use. Typical neutron reflectors contain berrylium, carobon, oxygen or bismuth, with the latter also having the advantage of being a good absorber of background gamma rays.

Making the sensitivity uniform along the source-detector direction is more difficult, because the neutron flux must be allowed to decrease substantially near the detector, although a neutron-absorbing gamma-ray window can reduce the required amount of this flux decrease as described in U.S. patent application, Ser. No. 808,103, filed on June 21, 1977 by the inventor herein. Fortunately in this direction solid-angle and gamma-ray-transmission effects tend to compensate for the flux variations reducing the sensitivity non-uniformities, although perfect cancellation of these effects can only be fortuitous. In addition as one of the techniques of this invention, the orientation of the source-detector line can be chosen to lie along the direction of minimum concentration variation, reducing the inaccuracies resulting from sensitivity changes within the measurement volume. A symmetrical configuration for the measurement volume will then facilitate the adjustment of the instrument orientation in order to obtain optimum accuracies for nonuniform materials flowing through the instrument.

The present invention has several features of novelty over the known prior art, including the use of a plurality of neutron sources and detectors, the presence of neutron reflectors and the proper choice of the configuration and orientation of the measurement volume, in order to obtain a uniform measurement sensitivity throughout the measurement volume so that segregated, inhomogeneous bulk materials can be measured accurately.

It is an object of this invention to provide an improvement in a neutron-capture-based, on-line, bulk-substance elemental-analyzer apparatus for obtaining uniformity of response throughout the measurement volume.

It is another object of this invention to provide an improvement in an elemental-analyzer apparatus of the foregoing type for making the apparatus insensitive to segregations that may occur in moving streams of the bulk substance being analyzed.

It is an additional object of this invention to provide an elemental analyzer of the foregoing type having a symmetrical chute which has rounded corners through which the bulk substance being analyzed flows to improve uniformity of measurement.

It is another object of this invention to provide an elemental analyzer of the foregoing type having multiple neutron sources located outside of the chute through which the bulk substance being analyzed passes to improve uniformity of measurement.

It is another object of this invention to provide in an elemental analyzer of the foregoing type the capability for accommodating the placement therein of a multiple number of detectors to improve uniformity of measurement.

It is a further object of this invention to surround the measurement volume of an elemental analyzer of the foregoing type with a neutron-reflecting material in order to improve the uniformity of measurement.

For a better undrestanding of the present invention, together with other and further objects thereof, reference is made to the following description taken in connection with the accompanying drawings in which preferred embodiments of the invention are illustrated, the scope of the invention being pointed out and contained in the appended claims.

BRIEF DESCRIPTION OF THE DRAWINGS

FIG. 1 shows a cross-sectional view of the neutron sources, the gamma-ray detector, the measurement volume, the shielding and other structure associated with a meter for the elemental analysis of coal, which forms a preferred embodiment of this invention.

FIG. 2 shows further details of the same instrument as that shown in FIG. 1, but in this case the sectional view has been taken along the line A—A in FIG. 1. The line B—B of FIG. 2 shows the sectioning line used for producing FIG. 1.

DESCRIPTION OF THE PREFERRED EMBODIMENTS

The application of these considerations to an apparatus for the elemental analysis of coal forms one of the preferred embodiments of this invention, as shown in FIGS. 1 and 2. Other embodiments involve the on-line measurement of coal-water mixtures, coal-oil mixtures, crude oil, fuel oil, gasoline, wheat and most other bulk substances containing some hydrogen. Thus, the portions of the preferred embodiment shown in FIGS. 1 and 2 which are specific to the measurement of coal are illustrative only and are not intended to limit the scope of this invention.

The instrument includes means for containing the bulk substance to be analyzed, which may flow through the instrument in order to provide a continuous, on-line measurement of bulk composition. In the embodiment shown in FIGS. 1 and 2, this means encloses the centrally-located measurement volume 18, in which the coal being analyzed is confined. Measurement volume 18 is the region throughout which the composition measurement takes place. Coal passing through the coal chute 40 continuously fills the measurement volume 18 with a current coal sample, facilitating the desired continuous, on-line bulk measurement.

In the embodiment of FIGS. 1 and 2, the means for containing the analyzed substance consists of the liner 36, which is partly surrounded by the bismuth gamma-ray shield 20. Because bismuth has a low probability for neutron absorption but does scatter neutrons, those portions of the gamma-ray shield 20 near the liner 36 reflect some of the escaping neutrons back into the measurement volume 18. As a result the gamma-ray shield 20 also acts as a neutron reflector, which increases the neutron flux along the sides of the measurement volume 18 in order to improve measurement uniformity and to use the neutrons more efficiently. Other elements besides bismuth are well known in the art to function as good neutron reflectors, including berrylium, oxygen, deuterium and carbon, and the use of any neutron-reflecting element for these purposes forms a part of this invention.

As shown in FIG. 1, the cross-section of the measurement volume 18 in the plane perpendicular to the flow of the bulk substance is a square with rounded corners. This symmetrical configuration provides several advantages compared to other configurations when measurement uniformity is important. First, this symmetry allows the instrument to be oriented easily such that the axis of the detector can lie along any desired direction without substantial modifications to the coal chute 40. Thus, the choice of the instrument orientation to minimize the sensitivity to composition segregations can be made relatively late in the installation process. Second, both the square cross section and the rounded corners exclude coal from regions of reduced measurement sensitivity. Because the configuration shown in FIG. 1 confines the coal to the region where neutron fluxes and detector 24 solid angles are relatively constant, the sensitivity throughout this plane will be more uniform than that provided by a wider measurement volume 18 or one permitting coal to enter square corners. These techniques also form a part of this invention, and they can be used separately or in combination with the other techniques described herein.

The instrument also includes neutron-producing means for providing neutrons. In the embodiment shown in FIG. 1, said neutron-producing means consists of two source capsules 10 and 12 containing the isotope Californium-252. In other embodiments of this invention the source could contain different isotopes, such as plutonium mixed with beryllium, or could contain a neutron generator, such as that using the $^3H(d,n)^4He$ reaction. Additionally the instrument could contain several other neutron sources, which could all be the same type or could be various combinations of source types. The neutronproducing means can be located either outside of the volume containing the bulk substance to be analyzed, as shown in FIGS. 1 and 2, or within this volume. If several neutron sources are present, some of these sources may be within this measurement volume, while other sources are external thereto. The principles forming a part of this invention apply to all of these variations of the embodiment shown in FIGS. 1 and 2.

The use of two neutron sources 10 and 12 as shown in FIG. 1 illustrates one of these principles. Because these two sources 10 and 12 are located near the corners of the measurement volume 18, the neutron flux is higher along the sides of the measurement volume 18 compared to its center. Because this flux increase compensates for the reduced detector 24 solid angle and gamma-ray transmission at the sides, the sensitivity uniformity is improved over the single-source case. Additional sources could be used to improve the uniformity even further, particularly if flow properties and flow rates of the bulk substance required a larger measurement volume 18 than that shown in FIG. 1.

In the embodiment of FIGS. 1 and 2 neutron moderators 14 and 16 surround the source capsules 10 and 12 in order to reduce neutron energies before the neutrons enter the measurement volume 18. A gamma-ray shield 20 then surrounds the moderators 14 and 16 to absorb gamma-rays produced by the source and the moderators and to provide a material with low neutron absorption through which neutrons can diffuse away from the source. The use of the moderators and gamma-ray shield is not essential to this invention, and their use in the embodiment shown in FIGS. 1 and 2 is not intended to limit the scope of the invention.

In the preferred embodiment shown in FIGS. 1 and 2, the neutron sources 10 and 12 are outside of the measurement volume 18, indicating that most neutrons will not enter the measurement volume 18. In order to control these unused escaping neutrons to avoid a radiation hazard and background in the measured energy spectrum, the preferred embodiment shown in FIGS. 1 and 2 includes the $^6LiH$ gamma-ray window 22, the boron-doped-polyethylene safety shields 38 and 32 with the source access rods 33 and 35, and the lithium in polyethylene 34. The existence of these neutron-absorbers in the preferred embodiment of FIGS. 1 and 2 is not intended to limit the scope of this invention.

In order to avoid a radiation hazard from escaping neutrons when the measurement volume 18 is empty, in the preferred embodiment the shield 32 on the detector side of the measurement volume 18 has been placed behind the sensor electronics 26 such that the gamma-ray detector 24 and the sensor electronics 26 are located with a chamber 37 in the neutron absorber. Even in this configuration some scattered radiation can leave the top and the bottom of the coal chute 40 passing through the measurement volume 18 when it is empty, because this region is not covered by shielding. A radiation alarm 42 and a movable plug 44 for the coal chute 40 when no coal is present provide the necessary protection to personnel when the coal chute is empty. If the movable plug 44 is constructed out of appropriate known materials, it can also be used for instrument calibration. The existence of the radiation alarm 42 and the movable plug 44 and the presence of a chamber 37 for the sensor electronics 26 in the preferred embodiment are not intended to limit the scope of this invention.

Some neutrons will diffuse through the gamma-ray shield 20 into the measurement volume 18. There hydrogen present in the coal being analyzed will moderate them further, and then they often will be captured by the various nuclei present in the analyzed coal. These neutron-capture reactions generally produce gamma ray, which travel through the measurement volume 18 and the neutron-absorbing gamma-ray window 22 and enter the gamma-ray detector 24, which in this embodiment forms a means for gamma-ray detection.

In the embodiment shown in FIGS. 1 and 2, this detector 24 is a large NaI(Tl) crystal, although other detectors such as CsI(Tl), CsI(Na), Ge or Ge(Li) could be used in instruments incorporating the features of this invention. For convenience, FIGS. 1 and 2 show a single detector 24, which is located near the side of the measurement volume 18 opposite the side near the source capsules 10 and 12, but this invention is not intended to be limited to the use of a single gamma-ray detector nor to its location across the measurement volume from the neutron source. In fact the use of a plurality of detectors with possibly some along the other sides of the measurement volume 18 would be beneficial in improving the measurement uniformity.

For example, multiple detectors placed at different points along the perimeter of the measurement volume 18 would provide a composite solid angle and gamma-ray transmission which are more uniform throughout the measurement volume 18 than those obtained with a single detector. As a result, measurement uniformity is improved, and in addition the total allowable counting rate, and thus the speed of response, become higher, because each detector can tolerate the same counting rate as a single detector. Such a multiple-detector array is particularly justified when high mass flow rates or other properties of the bulk substance result in a large measurement volume 18, which a single detector cannot view with sufficient uniformity. The combination of multiple detectors with multiple sources and/or neutron reflectors can improve the measurement uniformity still further, and the detectors could also be usefully placed along more than one side of the measurement volume.

When the gamma rays interact in the gamma-ray detector 24, they produce electrical signals indicative of their energy. The sensor electronics 26 convert these electrical signals into digital information, which is transmitted over an interconnecting cable 28 to the display console 30. The display console 30 processes this information using the fact that neutron capture produces an energy specturm which depends on the amounts of the various elements capturing the neutrons. The result of this processing is information concerning the relative concentrations of the various elements of interest in the measurement volume 18 and any other properties, such as density, which may be usefully obtained from the measured spectrum. The interface between the sensor electronics 26 and the display console 30 and the methods used therein also do not form a part of this invention.

What I claim as new is:

1. An improved apparatus for the on-line analysis of the composition of a bulk substance in a measurement volume, wherein said analysis includes the production and capture of neutrons and the detection of the resulting capture gamma rays, said apparatus comprising, in combination:
   (a) means for containing the bulk substance to be analyzed, said means comprising a bulk substance receiving passageway substantially square in cross-section having first, second, third and fourth interconnected sides said means for containing the bulk substance being at least partly surrounded by a neutron-reflecting substance;
   (b) neutron-producing means for providing neutrons which generate gamma rays by neutron-capture reactions with the nuclei in the bulk substance being analyzed, the neutron-producing means being operably associated with the means for containing the bulk substance; and
   (c) means for gamma-ray detection operably associated with the neutron-producing means and the means for containing the bulk substance being analyzed, the means for gammaray detection producing electrical signals indicative of the gamma-ray energies to provide for the measurement of the energy spectrum of the capture gamma rays.

2. An apparatus as defined in claim 1 in which said neutron-producing means comprises a pair of neutron sources located externally of said passageway near the corners of said first side thereof whereby the neutron flux produced is relatively higher along the sides of said passageway disposed perpendicular to said first side thereof as compared with that produced by one source diposed exteriorly of said passageway at a location equidistant from said corners of said first side.

3. An apparatus as defined in claim 1 in which said means for gamma ray detection comprises a plurality of gamma ray detectors located along the side of said passageway disposed opposite from the first side thereof and along the sides disposed adjacent to said first side of said passageway.

4. An improved apparatus for the on-line analysis of the composition of a bulk substance flowing through a measurement volume, wherein said analysis includes the production and capture of neutrons and the detection of the resulting capture gamma rays, said apparatus comprising, in combination:
   (a) means for containing the bulk substance to be analyzed, said means comprising an elongated passageway adapted to contain said bulk substance as it flows through said apparatus, said passageway being at least partly surrounded by a neutron-reflecting substance;
   (b) neutron-producing means for providing neutrons which generate gamma rays by neutron-capture reactions with the nuclei in the bulk substance being analyzed, said neutron-producing means comprising at least one neutron source located externally of said passageway;
   (c) means for gamma-ray detection operably associated with the neutron-producing means and the means for containing the bulk substance being analyzed, the means for gamma-ray detection producing electrical signals indicative of the gamma-ray energies to provide for the measurement of the energy spectrum of the capture gamma rays, said means comprising at least one gamma-ray detector disposed externally of said passageway.

5. An apparatus as defined in claim 4 including a plurality of neutron sources located externally of said passageway.

6. An apparatus as defined in claim 4 including a plurality of gamma ray detectors located externally of said passageway.

7. An apparatus as defined in claim 4 in which said passageway is substantially rectangular in cross-section wit the corners thereof rounded to direct the flow of the bulk substance toward said region of maximum sensitivity.

8. An apparatus as defined in claim 4 in which said passageway is substantially square in cross-section with the corners thereof rounded to direct the flow of the bulk substance toward said region of maximum sensitivity.

* * * * *

REEXAMINATION CERTIFICATE (4105th)

United States Patent [19]
Marshall

[11] B1 4,682,043
[45] Certificate Issued Jun. 27, 2000

[54] OBTAINING UNIFORMITY OF RESPONSE IN ANALYTICAL MEASUREMENT IN A NEUTRON-CAPTURE-BASED ON-LINE BULK-SUBSTANCE ELEMENTAL-ANALYZER

[75] Inventor: J. Howard Marshall, Pasadena, Calif.

[73] Assignee: Gamma-Metrics, San Diego, Calif.

Reexamination Request:
 No. 90/005,237, Jan. 28, 1999

Reexamination Certificate for:
 Patent No.: 4,682,043
 Issued: Jul. 21, 1987
 Appl. No.: 06/061,833
 Filed: Jul. 30, 1979

Related U.S. Application Data

[63] Continuation of application No. 05/866,488, Jan. 3, 1978.

[51] Int. Cl.$^7$ .................................................. G01N 23/222
[52] U.S. Cl. ................................... 250/358.1; 250/359.1; 250/390.04
[58] Field of Search ......................... 376/159; 250/359.1, 250/358.1, 390.04

[56] References Cited

U.S. PATENT DOCUMENTS

| | | | |
|---|---|---|---|
| 3,053,338 | 9/1962 | Tittle | 209/3.1 |
| 3,582,647 | 6/1971 | Figuet et al. | 378/52 |
| 3,832,545 | 8/1974 | Bartko. | |
| 4,152,596 | 5/1979 | Marshall, III. | |
| 4,171,485 | 10/1979 | Marshall. | |
| 4,266,132 | 5/1981 | Marshall, III. | |

OTHER PUBLICATIONS

Stewart, R.F. et al., "Nuclear Meter for Monitoring the Sulfur Content of Coal Streams," *Advancing Energy Utilization Program—Bureau of Mines Technical Progress Report,* Jan. 1974, TPR 74, Int.–Bureau of Mines, Pittsburgh, PA 19127.

Rhodes, J.R., "Neutron–Gamma Techniques for On–Stream Analysis of Coal," American Chemical Society Symposium *"New Techniques in Coal Analysis,"* Aug. 28–Sep. 7,1977, Chicago, IL.

Reynolds, G.M. et al., "4. System Optimization for Prompt–Neutron Activation Analysis of Coal," *Nuclear Techniques in Geology,* Transactions of the American Nuclear Society, 1977 Winter Meeting, Nov. 27–Dec. 2, 1977, San Francisco, CA.

(List continued on next page.)

*Primary Examiner*—Constantine Hannaher

[57] ABSTRACT

In an apparatus for neutron-capture-based on-line elemental analysis of bulk substances, an improved uniformity of response of analytical measurement will make the apparatus less sensitive to segregations that occur in moving streams of the bulk substance. The apparatus incorporates a measurement volume having a substantially-square cross-section with rounded corners in the plane perpendicular to the direction of flow in order to exclude the bulk substance from regions of unusual sensitivities and to facilitate the orientation of the instrument for minimum sensitivity to segregations in the bulk substance. The apparatus also includes a plurality of neutron sources which expose the analyzed bulk substance momentarily contained within the apparatus to a flux of neutrons. The apparatus also provides for the use of neutron reflectors to increase the neutron flux near the sides of the measurement volume, further improving the uniformity of measurement. The analyzed substance captures some of the neutrons by (n,γ) reactions, producing prompt gamma rays which are detected to provide the composition measurement. The use of multiple sources causes the neutron flux to rise instead of fall near the sides of the volume containing the bulk substance compared to the center of the volume, and flux variations can be made to cancel solid-angle variations to produce a more-uniform response over a substantial portion of the measurement volume. Similarly the use of multiple gamma-ray detectors can also reduce these solid-angle variations, improving measurement uniformity, particularly if the measurement volume is large because of material-flow requirements.

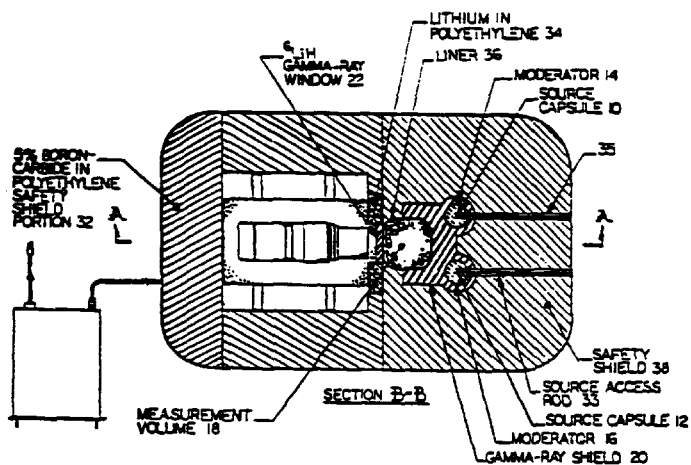

OTHER PUBLICATIONS

Mihai Borsaru and Ralph J. Holmes, "Determination of Aluminum in Bulk Ore Samples by Neutron Activation Analysis." *Analytical Chemistry,* vol. 48, No. 12, pp. 1699–1701. Oct. 1976.

J. R. Rhodes, P. F. Berry, and R. D. Sieberg, "Nuclear Techniques in On–Stream Analysis of Ores and Coal." (Report), ORO–2980–18, for Division of Isotopes Development, United States Atomic Energy Commission, pp. 1–88. Sep. 1968.

T. Gozani et al., "Coal Stream Composition Analysis for Porcess [sic] Control Using Prompt Neutron Activation Analysis," Proceedings of the 1977 Symposium on Instrumentation and Process Control for Fossil Demonstration Plants, Jul. 13–15, 1977, Chicago, Illinois, published as Argonne National Laboratory, Illinois Publication No. ANL–78–7, 1977, pp. 162–193.

Anonymous, "Field Analysis Technique for Plastic Concrete," *California–252 Progress,* No. 17 (May 1974) pp. 17–20.

Anonymous, "Dartmouth College," *California–252 Progress,* No. 11 (Apr. 1972) pp. 42–43.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 11–29:

One technique often used in industrial environments for elemental analysis involves X-ray [fluoresence] *fluorescence*. This technique relies on the fact that each atom emits X-rays with distinct and well-known energies when external radiations disturb its orbital electrons. Unfortunately, sulfur, which is an interesting element from the standpoints of air pollution and catalyst poisoning, emits mostly 2-keV X-rays, which can only traverse about 0.1 mm of a typical fuel. Iron, which is one of the elements generating the highest-energy X-rays in coal, produces mostly a 6-keV X-ray, which also cannot escape from any appreciable amount of coal or other nongaseous fuel. Thus, the use of X-ray fluorescence for other than gaseous materials requires either the preparation of very clean surfaces truly representative of the bulk material or the vaporization of a sample in an atmosphere which does not confuse the measurement. In either case, a difficult sample-preparation problem compounds the errors associated with X-ray fluorescence itself.

Column 2, lines 48–59:

Nonetheless, nuclear techniques in general remain attractive because they often can be automated and in principal do not require actual manipulation of the bulk material itself. The problems with X-ray fluorescence and absorption arise partly because the [Associated] *associated* radiations are not sufficiently penetrating. However, because the energenic gamma rays produced by the capture of thermal neutrons will penetrate over 100 mm of most fuels, an analysis technique based on them can provide an accurate, continuous, on-line measurement of the elemental composition of bulk substances without sampling.

Column 3, lines 7–19:

The above emphasis on thermal neutrons reflects the fact that for most elements the cross section for neutron capture is [approxiately] *approximately* proportional to the reciprocal of the square root of the neutron energy. Thus, almost all neutron capture occurs at the lowest neutron energies, which happen when the neutrons are in thermal equilibrium with the nuclei of the [surrouding] *surrounding* medium. As a result, the thermal-neutron-capture cross sections characterize the expected prompt-gamma-ray spectra. These gamma-ray spectra are particularly amenable to simple theoretical interpretation using well-known thermal-neutron-capture cross sections, making automatic operation a feasible concept.

Column 4, lines 30–43:

In these prior-art instruments all of these [effective] *effectively* combined to make the sensitivity at the side of the chute on the opposite side of the source as the detector considerably less than the sensitivity in the volume between the source and the detector. However, if the neutron source is located outside of the measurement volume as described in another application for a U.S. patent, Ser. No. 808,106, filed on June 21, 1977 by the inventor herein, then the measurement can be confined to the volume between the source and the detector, resulting in improved uniformity. However, unless the techniques of this invention are also employed, the uniformity of sensitivity may still be insufficient to measure accurately segregated, inhomogeneous substances.

Column 5, lines 18–32:

The flux at the sides of the measurement volume can be increased by still other means. For example, a smaller measurement volume has a smaller sensitivity variation than one with a larger cross-sectional area. Eliminating low-sensitivity regions, such as the corners of a coal chute, from the measurement volume also improves uniformity. In addition surrounding the measurement volume with a material which scatters neutrons without absorbing many of them will reflect neutrons back into the measurement volume, thus increasing the flux at the sides and improving the efficiency of neutron use. Typical neutron reflectors contain [berrylium, carobon] *beryllium, carbon*, oxygen or bismuth, with the latter also having the advantage of being a good absorber of background gamma rays.

Column 5, lines 33–54:

Making the sensitivity uniform along the source-detector direction is more difficult, because the neutron flux must be allowed to decrease substantially near the detector, although a neutron-absorbing gamma-ray window can reduce the required amount of this flux decrease as described in U.S. [patent application, Ser. No. 808,103] *Patent No. 4,266,132*, filed on June [21] *20*, 1977 by the inventor herein. Fortunately in this direction solid-angle and gamma-ray-transmission effects tend to compensate for the flux variations reducing the sensitivity non-uniformities, although perfect cancellation of these effects can only be fortuitous. In addition as one of the techniques of this invention, the orientation of the source-detector line can be chosen to lie along the direction of minimum concentration variation, reducing the inaccuracies resulting from sensitivity changes within the measurement volume. A symmetrical configuration for the measurement volume will then facilitate the adjustment of the instrument orientation in order to obtain optimum accuracies for nonuniform materials flowing through the instrument.

Column 6, lines 25–31:

For a better [undrestanding] *understanding* of the present invention, together with other and further objects thereof, reference is made to the following description taken in connection with the accompanying drawings in which preferred embodiments of the invention are illustrated, the scope of the invention being pointed out and contained in the appended claims.

Column 7, lines 3–19:

In the embodiment of FIGS. 1 and 2, the means for containing the analyzed substance consists of the liner 36, which is partly surrounded by the bismuth gamma-ray shield 20. Because bismuth has a low probability for neutron absorption but does scatter neutrons, those portions of the gamma-ray shield 20 near the liner 36 reflect some of the escaping neutrons back into the measurement volume 18. As a result the gamma-ray shield 20 also acts as a neutron reflector, which increases the neutron flux along the sides of the measurement volume 18 in order to improve measurement uniformity and to use the neutrons more efficiently. Other elements besides bismuth are well known in the art to function as good neutron reflectors, including [berrylium] *beryllium*, oxygen, deuterium and carbon, and the use of any neutron-reflecting element for these purposes forms a part of this invention.

Column 7, lines 43–62:

The instrument also includes neutron-producing means for providing neutrons. in the embodiment shown in FIG. 1, said neutron-producing means consists of two source capsules 10 and 12 containing the isotope. Californium-252. In other embodiments of this invention the source could contain different isotopes, such as plutonium mixed with beryllium, or could contain a neutron generator, such as that using the $^3$H(d,n)$^4$He reaction. Additionally the instrument could contain several other neutron sources, which could all be the same type or could be various combinations of source types. The [neutronproducing] *neutron producing* means can be located either outside of the volume containing the bulk substance to be analyzed, as shown in FIGS. 1 and 2, or within this volume. If several neutron sources are present, some of these sources may be within this measurement volume, while other sources are external thereto. The principles forming a part of this invention apply to all of these variations of the embodiment shown in FIGS. 1 and 2.

Column 9, lines 29–45:

When the gamma rays interact in the gamma-ray detector 24, they produce electrical signals indicative of their energy. The sensor electronics 26 convert these electrical signals into digital information, which is transmitted over an interconnecting cable 28 to the display console 30. The display console 30 processes this information using the fact that neutron capture produces an energy [specturm] *spectrum* which depends on the amounts of the various elements capturing the neutrons. The result of this processing is information concerning the relative concentrations of the various elements of interest in the measurement volume 18 and any other properties, such as density, which may be usefully obtained from the measured spectrum. The interface between the sensor electronics 26 and the display console 30 and the methods used therein also do not form a part of this invention.

AS A RESULT OF REEXAMINATION, IT HAS BEEN DETERMINED THAT:

Claims 1, 2, 4 and 7 are determined to be patentable as amended.

Claims 3, 5, 6 and 8, dependent on an amended claim, are determined to be patentable.

New claims 9–17 are added and determined to be patentable.

1. An [improved] apparatus for the on-line analysis of the composition of a bulk substance in a measurement volume, wherein said analysis includes the production and capture of neutrons and the detection of the resulting capture gamma rays, said apparatus comprising, in combination:
   (a) means for containing the bulk substance to be analyzed, said means comprising a bulk substance receiving passageway substantially square in cross-section having first, second, third and fourth interconnected sides said means for containing the bulk substance being at least partly surrounded by a neutron-reflecting substance;
   (b) neutron-producing means for providing neutrons which generate gamma rays by neutron-capture reactions with the nuclei in the bulk substance being analyzed, the neutron-producing means being operably associated with the means for containing the bulk substance; and
   (c) means for gamma-ray detection operably associated with the neutron-producing means and the means for containing the bulk substance being analyzed, the means for [gammaray] *gamma ray* detection producing electrical signals indicative of the gamma-ray energies to provide for the measurement of the energy spectrum of the capture gamma rays.

2. An apparatus as defined in claim 1 in which said neutron-producing means comprises a pair of neutron sources located externally of said passageway near the corners of said first side thereof whereby the neutron flux produced is relatively higher along the sides of said passageway disposed perpendicular to said first side thereof as compared with that produced by one source [diposed] *disposed* exteriorly of said passageway at a location equidistant from said corners of said first side.

4. An [improved] apparatus for the on-line analysis of the composition of a bulk substance flowing through a measurement volume, wherein said analysis includes the production and capture of neutrons and the detection of the resulting capture gamma rays, said apparatus comprising, in combination:
   (a) means for containing the bulk substance to be analyzed, said means comprising an elongated passageway adapted to contain said bulk substance as it flows through said apparatus, said passageway being at least partly surrounded by a neutron-reflecting substance;
   (b) neutron-producing means for providing neutrons which generate gamma rays by neutron-capture reactions with the nuclei in the bulk substance being analyzed, said neutron-producing means comprising at least one neutron source located externally of said passageway;
   (c) means for gamma-ray detection operably associated with the neutron-producing means and the means for containing the bulk substance being analyzed, the means for gamma-ray detection producing electrical signals indicative of the gamma-ray energies to provide for the measurement of the energy spectrum of the capture gamma rays, said means comprising at least one gamma-ray detector disposed externally of said passageway.

7. An apparatus as defined in claim 4 in which said passageway is substantially rectangular in cross-section [wit] *with* the corners thereof rounded to direct the flow of the bulk substance toward said region of maximum sensitivity.

9. *An apparatus for on-line elemental analysis of a bulk substance comprising a plurality of elements flowing through a measurement volume within the apparatus, the apparatus comprising:*
   *an elongated passageway extending through the apparatus, the passageway adapted to enclose the measurement volume and direct the bulk substance flowing through the measurement volume;*
   *a neutron-reflecting substance at least partially surrounding the passageway adjacent the measurement volume;*
   *at least one neutron source disposed external to a source side of the passageway for providing thermal neutrons which interact with nuclei of the elements in the bulk substance within the measurement volume to generate prompt gamma rays having a plurality of energies; and* at least one gamma ray detector disposed external to a detector side of the passageway opposite the source side, the gamma ray detector producing electrical signals indicative of the plurality of energies of the prompt gamma rays to provide for measurement of an energy spectrum of the prompt gamma rays corresponding to the plurality of elements within the bulk material.

10. The apparatus of claim 9, wherein the measurement volume has a four-cornered cross-section and the at least one neutron source comprises two neutron source capsules disposed at locations corresponding to two corners of the measurement volume on the source side of the passageway, each source capsule containing a neutron-producing isotope.

11. The apparatus of claim 10, wherein the neutron-producing isotope is californium-252.

12. The apparatus of claim 9, wherein the at least one neutron sources comprises a neutron generator.

13. The apparatus of claim 9, wherein the at least one detector comprises a multi-detector array.

14. The apparatus of claim 13, where the multi-dectector array comprises at least two sodium iodide crystals.

15. The apparatus of claim 9, wherein the neutron-reflecting substance is selected from the group consisting of bismuth, beryllium, oxygen, deuterium and carbon.

16. The apparatus of claim 9, wherein the passageway is a chute having a substantially square cross-section.

17. The apparatus of claim 9, wherein the passageway is a chute having a substantially rectangular cross-section.

* * * * *